US00PP28261P2

(12) United States Plant Patent
Beekenkamp

(10) Patent No.: US PP28,261 P2
(45) Date of Patent: Aug. 8, 2017

(54) ***CAMPANULA* PLANT NAMED 'BKPCMPKY'**

(50) Latin Name: *Campanula portenschlagiana*
Varietal Denomination: BKPCMPKY

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 14/999,402

(22) Filed: May 3, 2016

(51) Int. Cl.
*A01H 5/02* (2006.01)

(52) U.S. Cl.
USPC ..... Plt./414

(58) Field of Classification Search
USPC ..... Plt./414
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Campanula* plant named 'BKPCMPKY' characterized by its compact, upright to outwardly spreading plant habit; freely branching habit; early and freely flowering habit; campanulate-shaped flowers with bright purple violet to violet-colored petals; and good garden performance.

2 Drawing Sheets

Botanical designation: *Campanula portenschlagiana.*
Cultivar denomination: 'BKPCMPKY'.

BACKGROUND OF THE INVENTION

The present invention relates to a new and distinct cultivar of *Campanula* plant, botanically known as *Campanula portenschlagiana*, commonly known as Dalmatian Bellflower and hereinafter referred to by the name 'BKPCMPKY'.

The new *Campanula* is a product of a planned breeding program conducted by the Inventor in Maasdijk, The Netherlands. The objective of the breeding program is to create new freely flowering *Campanula* plants with attractive flowers and good interior and garden performance.

The new *Campanula* plant originated from a cross-pollination conducted by the Inventor in Maasdijk, The Netherlands in April, 2012 of a proprietary selection of *Campanula portenschlagiana* identified as code number 4400320, not patented, as the female, or seed, parent with a proprietary selection of *Campanula portenschlagiana* identified as code number 4400319, not patented, as the male, or pollen, parent. The new *Campanula* plant was discovered and selected by the Inventor as a single flowering plant from within the progeny of the stated cross-pollination grown in a controlled outdoor nursery in Maasdijk, The Netherlands in May, 2013.

Asexual reproduction of the new *Campanula* plant by terminal cuttings in Maasdijk, The Netherlands, since February, 2014 has shown that the unique features of this new *Campanula* plant are stable and reproduced true to type in successive generations.

SUMMARY OF THE INVENTION

Plants of the new *Campanula* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BKPCMPKY'. These characteristics in combination distinguish 'BKPCMPKY' as a new and distinct *Campanula* plant:

1. Compact, upright to outwardly spreading plant habit.
2. Freely branching habit.
3. Early and freely flowering habit.
4. Campanulate-shaped flowers with bright purple violet to violet-colored petals.
5. Good garden performance.

Plants of the new *Campanula* differ from plants of the female parent selection in the following characteristics:

1. Plants of the new *Campanula* are more upright than plants of the female parent selection.
2. Plants of the new *Campanula* flower earlier than plants of the female parent selection.
3. Plants of the new *Campanula* are more freely flowering than plants of the female parent selection.

Plants of the new *Campanula* differ from plants of the male parent selection in the following characteristics:

1. Plants of the new *Campanula* are more upright than plants of the male parent selection.
2. Plants of the new *Campanula* flower earlier than plants of the male parent selection.
3. Plants of the new *Campanula* and the male parent selection differ in flower color as plants of the male parent selection have dark blue-colored flowers.

Plants of the new *Campanula* can be compared to plants of *Campanula portenschlagiana* 'Get Mee', not patented. In side-by-side comparisons, plants of the new *Campanula* differ primarily from plants of 'Get Mee' in the following characteristics:

1. Plants of the new *Campanula* are more upright than plants of 'Get Mee'.
2. Plants of the new *Campanula* are more freely flowering than plants of 'Get Mee'.

3. Plants of the new *Campanula* flower earlier than plants of 'Get Mee'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the colors of the new *Campanula* plant.

The photograph on the first sheet is a side perspective view of a typical flowering plant of 'BKPCMPKY' grown in a container.

The photograph on the second sheet is a close-up view of a typical flowering plant of 'BKPCMPKY'.

DETAILED BOTANICAL DESCRIPTION

Plants used for the aforementioned photographs and following description were grown during the winter in 12-cm containers in a glass-covered greenhouse in Maasdijk, The Netherlands and under cultural practices typical of commercial production conditions. During the production of the plants, day temperatures ranged from 15° C. to 19° C. and night temperatures ranged from 14° C. to 16° C. Plants were 15 weeks old when the photographs and description were taken. In the following description, color references are made to The Royal Horticultural Society Colour Chart, 2015 Edition, except where general terms of ordinary dictionary significance are used.

Botanical classification: *Campanula portenschlagiana* 'BKPCMPKY'.

Parentage:

*Female, or seed, parent*.—Proprietary selection of *Campanula portenschlagiana* identified as code number 4400320, not patented.

*Male, or pollen, parent*.—Proprietary selection of *Campanula portenschlagiana* identified as code number 4400319, not patented.

Propagation:

*Type*.—By terminal cuttings.

*Time to initiate roots, summer*.—About 21 days at temperatures about 19° C. to 21° C.

*Time to produce a rooted young plant, summer*.—About 26 days at temperatures about 19° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; compact, upright to outwardly spreading plant habit; flattened globular in shape; moderately vigorous growth habit; moderate growth rate.

*Plant height, soil level to top of foliar plane*.—About 12.8 cm.

*Plant height, soil level to top of floral plane*.—About 16.5 cm.

*Plant width*.—About 29.3 cm.

*Lateral branch description*.—Branching habit: Freely branching habit with about 35 primary branches each with two secondary branches developing per plant. Aspect: Upright to prostrate, ranging from about 0° to 90° from vertical. Length: About 8.7 cm. Diameter: About 2 mm. Internode length: About 1.3 cm. Strength: Moderately strong. Texture and luster: Smooth, glabrous; glossy. Color, developing: Close to 144A. Color, developed: Close to 143B to 143C.

Leaf description:

*Arrangement*.—Alternate, simple.

*Length*.—About 2.2 cm.

*Width*.—About 3 cm.

*Shape*.—Reniform.

*Apex*.—Broadly acute.

*Base*.—Reniform to broadly attenuate.

*Margin*.—Coarsely and irregularly dentate.

*Texture and luster, upper surface*.—Smooth, glabrous; slightly glossy.

*Texture and luster, lower surface*.—Smooth, glabrous; matte.

*Venation pattern*.—Pinnate.

*Color*.—Developing leaves, upper surface: Close to between 139A and 147A. Developing leaves, lower surface: Close to 137B. Fully developed leaves, upper surface: Close to between 139A and 147A; venation, close to 143A to 143B. Fully developed leaves, lower surface: Close to NN137D; venation, close to 144A.

*Petioles*.—Length: About 4.3 cm. Diameter: About 1 mm. Texture and luster, upper and lower surfaces: Smooth, glabrous; glossy. Color, upper surface: Close to between 143C and 144C. Color, lower surface: Close to 144B to 144C.

Flower description:

*Flower arrangement and shape*.—Single campanulate flowers arranged in axillary and terminal cymes; flowers face upright to slightly outwardly; freely flowering habit with about six flowers developing per inflorescence and about 1,000 flowers developing per plant during the flowering season.

*Natural flowering season*.—Early flowering habit; plants begin flowering about 105 days after planting; in the garden, flowering continuous from spring into the autumn in The Netherlands.

*Flower longevity on the plant*.—About four weeks; flowers persistent.

*Fragrance*.—None detected.

*Inflorescence height*.—About 11.1 cm.

*Inflorescence diameter*.—About 7.1 cm.

*Flower buds*.—Length: About 1.2 cm. Diameter: About 7 mm. Shape: Oblong. Texture and luster: Smooth, glabrous; glossy. Color: Close to 83C; ribs, close to N82C to N82D.

*Flower diameter*.—About 2.2 cm.

*Flower length (height)*.—About 1.5 cm.

*Flower tube diameter, distally*.—About 1 cm.

*Flower tube length*.—About 8 mm.

*Petals*.—Quantity and arrangement: Five in a single whorl; lower 55% of petal length fused. Length: About 1.7 cm. Width, at the base of the free part of the petal: About 6 mm. Shape: Oblanceolate. Apex: Acute. Margin: Entire. Texture and luster, upper surface: Smooth, glabrous; slightly velvety; matte. Texture and luster, lower surface: Smooth, glabrous; slightly velvety; slightly glossy. Color: When opening, upper surface: Close to N87B. When opening, lower surface: Close to N87D. Fully opened, upper surface: Close to between N82A and N87A; color does not fade with development. Fully opened, lower surface: Close to N87B; color does not fade with development. Flower tube: Slightly lighter than 86D.

*Sepals*.—Quantity and arrangement: Five in a single campanulate whorl. Length: About 4 mm. Width: About 1 mm. Shape: Narrowly oblong to lanceolate. Apex: Acute. Base: Broadly cuneate. Margin: Entire. Texture and luster, upper surface: Smooth, glabrous; matte. Texture and luster, lower surface: Smooth, glabrous; slightly glossy. Color: When developing, upper surface: Close to 137D. When developing, lower surface: Close to 138B. Fully developed, upper surface: Close to 137D. Fully developed, lower surface: Close to 138A.

*Peduncles*.—Length: About 8.7 cm. Diameter: About 1.5 mm. Aspect: Terminal inflorescences, upright; axillary inflorescences, about 40° from stem axis. Strength: Moderately strong. Texture and luster: Smooth, glabrous; glossy. Color: Close to 143C.

*Pedicels*.—Length: About 1.5 cm. Diameter: About 8 mm. Aspect: Terminal flowers, upright; axillary flowers, about 40° from peduncle axis. Strength: Moderately strong. Texture and luster: Smooth, glabrous; glossy. Color: Close to 143C.

*Reproductive organs*.—Stamens: Quantity per flower: Five. Filament length: About 1 mm. Filament color: Close to NN155D. Anther length: About 4 mm. Anther shape: Narrowly oblong. Anther color: Close to 8C. Pollen amount: Scarce to moderate. Pollen color: Close to 4D. Pistils: Quantity per flower: One. Pistil length: About 8 mm. Stigma diameter: About 3 mm. Stigma shape: Decurrent; three-parted. Stigma color: Close to 85C. Style length: About 6.5 mm. Style color: Close to 85B. Ovary color: Close to 144A.

*Seeds and fruits*.—Seed and fruit production have not been observed on plants of the new *Campanula*.

Disease & pest resistance: Plants of the new *Campanula* have not been observed to be resistant to pathogens and pests common to *Campanula* plants.

Garden performance: Plants of the new *Campanula* have exhibited good tolerance to rain, wind and temperatures ranging from about −35° C. to about 35° C. and to be suitable for USDA Hardiness Zones 3 to 9.

It is claimed:

1. A new and distinct *Campanula* plant named 'BKPC-MPKY' as illustrated and described.

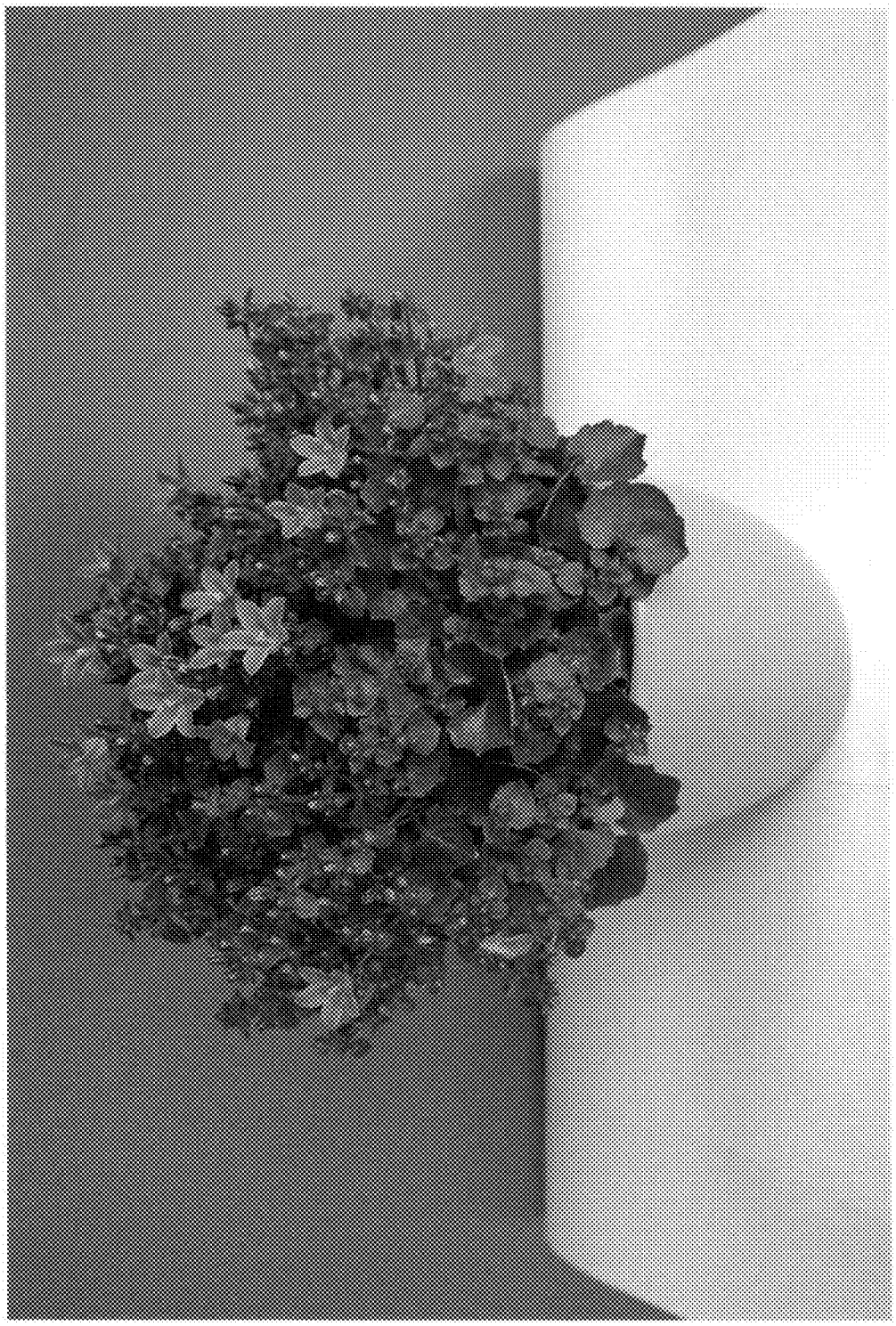

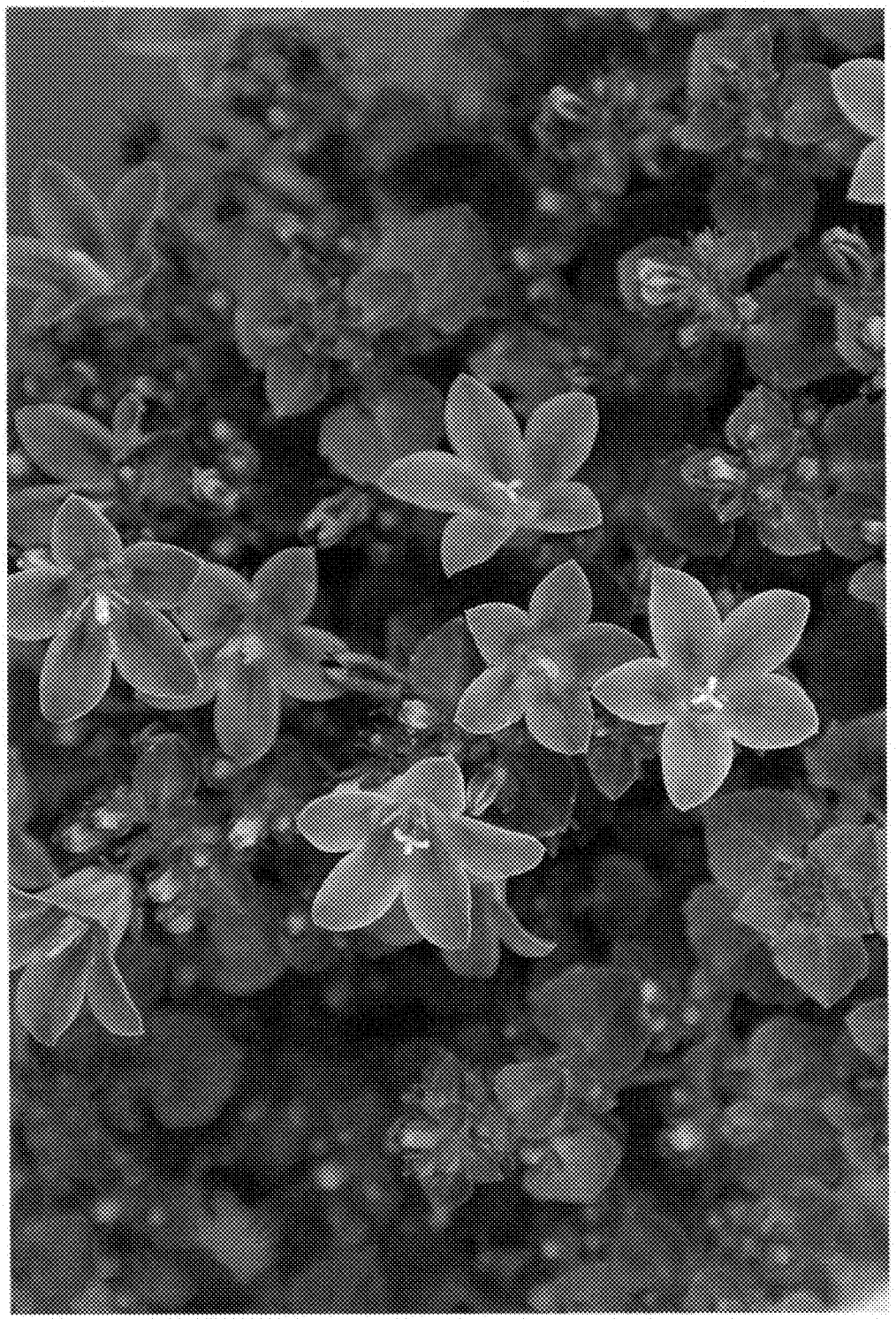

* * * * *